United States Patent [19]

Cutter

[11] 4,443,888
[45] Apr. 17, 1984

[54] SID MONITOR

[75] Inventor: James W. Cutter, Hollister, Calif.

[73] Assignee: Litton Industrial Products, Inc., Beverly Hills, Calif.

[21] Appl. No.: 362,808

[22] Filed: Mar. 29, 1982

[51] Int. Cl.³ .......................... G03B 41/16; G01B 5/02
[52] U.S. Cl. .................................. 378/151; 33/125 R
[58] Field of Search ............. 33/125 R; 378/150, 151, 378/91

[56] References Cited

U.S. PATENT DOCUMENTS

| | | | |
|---|---|---|---|
| 2,293,730 | 8/1942 | Guttmann | 33/125 R |
| 2,293,733 | 8/1942 | Guttmann | 33/125 R |
| 3,566,477 | 3/1971 | Williams | 33/125 R |
| 3,581,094 | 5/1971 | Peyser . | |
| 3,863,073 | 1/1975 | Wagner | 378/150 |
| 3,936,943 | 2/1976 | Bullard | 33/125 R |

OTHER PUBLICATIONS

*Machlett Technical Manual, St-3450 Collimaster, C,* Machlett Labs. Inc., Stamford Ct., pp. 1, 10, 35 & FIG. 5-2.

Primary Examiner—Alfred E. Smith
Assistant Examiner—T. N. Grisby
Attorney, Agent, or Firm—John M. Haurykiewicz; Walter R. Thiel

[57] ABSTRACT

An improvement in Source-to-Image Distance monitors for automatic adjusting X-ray radiography equipment having a cable, rewind spring, a self-traversing constant diameter takeup drum moving past a fixed aperture, an electrical potentiometer to provide a continuously varying electrical output signal and a snap action switch mechanism to indicate relative movement of the X-ray apparatus being monitored.

9 Claims, 6 Drawing Figures

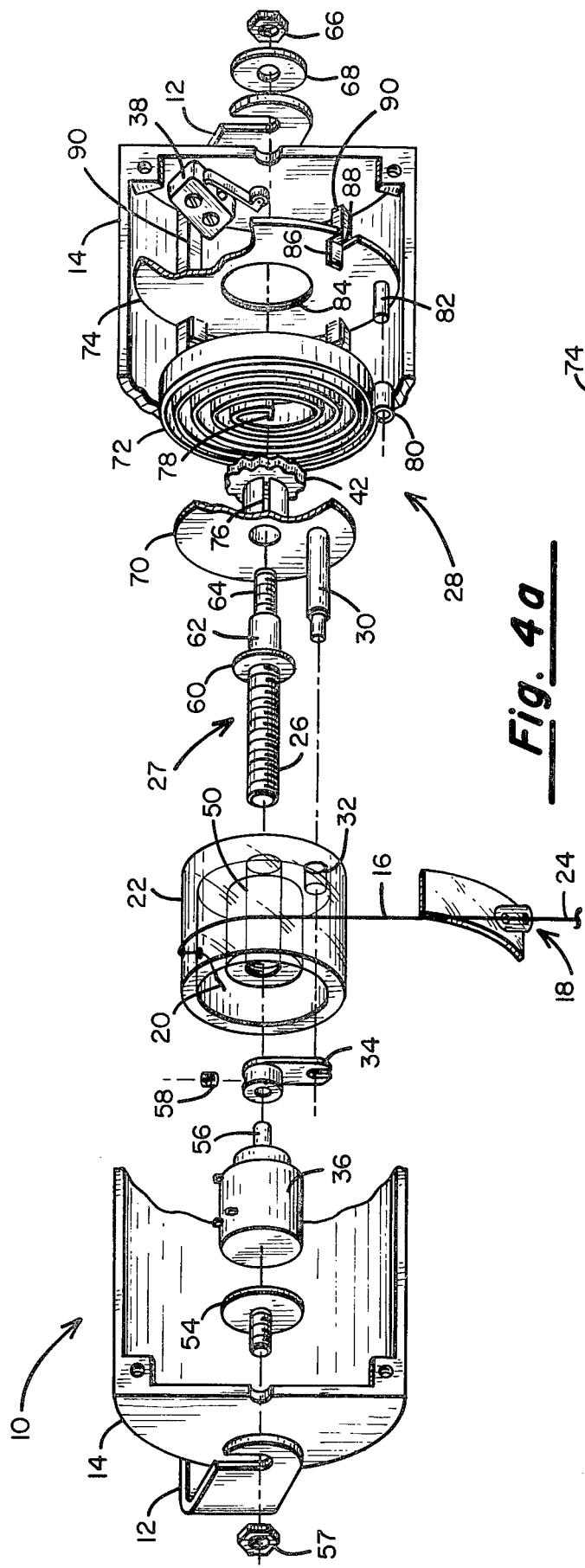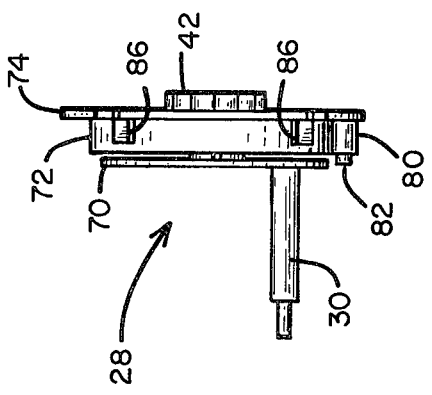

SID MONITOR

BACKGROUND OF THE INVENTION

In the past, attempts have been made to provide devices to transduce the source to image distance (SID) for automatic X-ray radiography equipment. Even though the need for such devices has increased due to increasing automation of such equipment and increasing restrictions in government regulations, prior art SID monitors have exhibited less than ideal characteristics. One approach to meeting this need has been to provide a transducer utilizing a cable wound onto a grooved rewind drum or reel by means of a guide roller riding in the groove ahead of the cable. The linear motion to be measured is converted by the linear motion of the cable into angular or rotational motion of the drum which is then easily transduced by means of an electrical potentiometer having an output proportional to the angular displacement of its moveable element. In this type of SID monitor, a wide guide or slot was provided in the housing to allow the cable and guide roller to traverse across the grooved drum. Other SID monitors have not provided for level winding, that is winding at a constant diameter, and hence have failed to accurately convert linear into rotary motion, which resulted in an inaccurate source to image distance signal. Still other approaches to providing a SID monitor included running a pinion gear against a rack to translate linear into rotary motion which was then converted into an appropriate electrical signal. Such a gear system resulted in a complicated, costly apparatus which required careful alignment and which was subject to becoming jammed or broken in the event a foreign object was interposed between the pinion and rack.

BRIEF SUMMARY OF THE INVENTION

The object of this invention is to meet the needs for a simple, inexpensive and reliable SID monitor, this invention provides a self-traversing, constant-diameter takeup cylinder which receives a torque from a takeup spring while being required to move in a helical motion past a fixed aperture to allow a wire moving through the aperture to be wound in a single layer on the cylinder.

According to another aspect of the invention a continuous source to image distance transducer is provided which has a cable attached within the transducer at one end and to a relatively moveable portion of the X-ray equipment at its other end, a rewind spring to maintain cable tension, a housing having a fixed aperture therein which is adapted to permit the cable to move longitudinally through the aperture and which prevents transverse displacement of the cable within the housing in the event of transverse displacement of the cable outside the housing, and a smooth surfaced drum to level wind the cable by combined rotation and translation of the drum with respect to the aperture.

BRIEF DESCRIPTION OF THE DRAWINGS

FIG. 4a is an exploded view of the components of this invention.

FIG. 4b is a side view of the rewind spring assembly.

DETAILED DESCRIPTION

Figure 1:
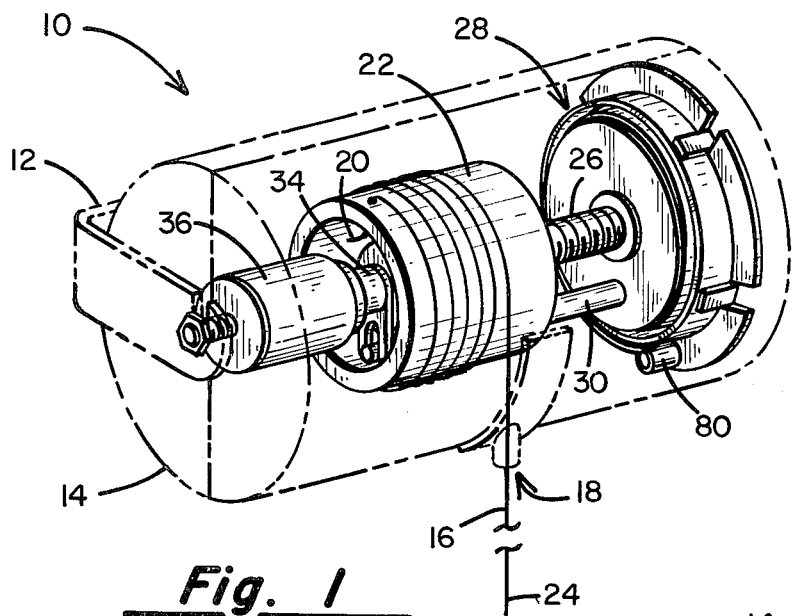
FIG. 1 discloses a perspective view of the assembly of this invention.

Referring to FIG. 1, the SID monitor or transducer 10 of this invention is shown. Transducer 10 is preferably mounted to a stationary portion of the X-ray apparatus (not shown) with which it is associated by means of mounting bracket 12. Transducer 10 is contained within a housing 14 shown only in outline form in FIG. 1. A cable or wire 16 passes through a fixed aperture 18 in housing 14 and is secured at one end 20 to a drum 22 and at the other end 24 to a relatively moveable portion of the X-ray apparatus (not shown). In a preferred embodiment environment, end 24 is secured to a moveable X-ray source, while transducer 10 is fixed with respect to the X-ray image or film plane (not shown). As the X-ray source is moved, cable 16 will move in correspondence to the change in the source to image distance of the associated X-ray apparatus and provide an electrical signal output varying continuously in proportion to the changing source to image distance.

Drum 22 is mounted on and is free to threadably engage a threaded portion 26 of shaft 27. Shaft 27 is stationary and secured to housing 14.

A rewind spring mechanism 28 is concentrically located and is free to rotate about a smooth section of shaft 27 and is pretensioned to provide torque about shaft 27 with respect to housing 14 by means of an eccentric crank 30. Crank 30 engages drum 22 by passing through an eccentric hole 32 (see FIGS. 3a and 3b) in drum 22 and also engages an arm 34 coupled to the moveable element of electrical potentiometer 36. The body of electrical potentiometer 36 is secured to housing 14 and is preferably in axial alignment with drum 22 and shaft 27. Rewind spring mechanism 28 thus tensions cable 16 by applying its torque to drum 22 through crank 30.

Figure 2:
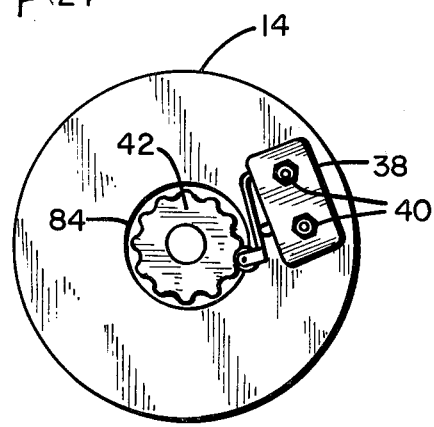
FIG. 2 shows an end view of details of the assembly of this invention not visible in FIG. 1.

Referring now more particularly to FIG. 2, an end view of the remaining components of transducer 10 may be seen. Housing 14 is again shown only in outline form. Snap action switch 38 is mounted by means of conventional hardware 40 to housing 14. Switch 38 is toggled by a rotating starwheel 42. Starwheel 42 is secured to and rotates with the portion of mechanism 28 to which crank 30 is secured. In the preferred embodiment, switch 38 has a moveable contact and a normally opened and a normally closed contact. The normally opened and normally closed contacts are preferably shorted electrically together and brought out by a conventional electrical lead as is the moveable contact. In operation, switch 38 provides a series of momentary open pulses as it is toggled by starwheel 42 and indicates to the associated X-ray control circuit (not shown) that the source to image distance of the associated X-ray apparatus is changing.

Figure 3A:
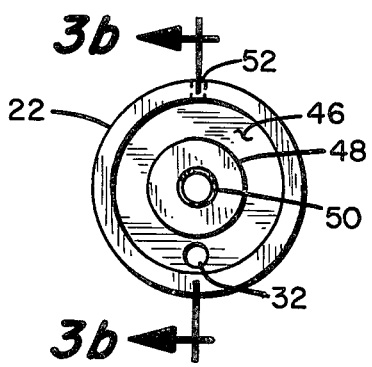
FIGS. 3a and 3b show respectively an end and sectional view of the rewind drum.
Figure 3B:
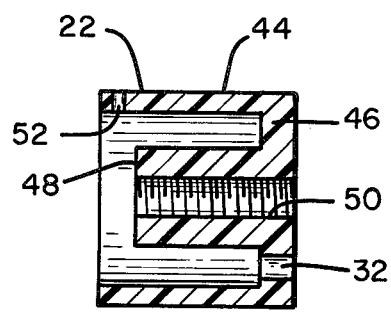

Referring now more particularly to FIGS. 3a and 3b, details of rewind drum or takeup cylinder 22 may be seen in end and section views. Drum 22 has a smooth or flat outer cylindrical surface 44 connected by a web 46 to a hub 48. Surface 44 is concentric to a threaded bore 50. An eccentric hole 32 is provided in web 46 to receive eccentric crank 30. A radially oriented hole 52 is provided in the outer surface 44 of drum 22 to receive and secure cable end 20.

Referring now more particularly to FIG. 4a, the various components of transducer 10 may be seen in more detail. Although potentiometer 36 may be secured to case 14 in any conventional manner, FIG. 4a shows potentiometer 36 mounted by means of a suitable adhesive such as epoxy to a threaded boss or pad 54 which is suitably secured to case 14 as for example, by nut 56. Shaft 56 operates the moveable element of potentiometer 36 and is coupled to eccentric crank 30 by arm 34. Arm 34 is secured to shaft 56 by a conventional set screw 58. Potentiometer 36 is a multi-turn type with number of turns preferably at least equal to the designed number of wraps of cable 16 on drum 22 when cable 16 is fully retracted into housing 14.

As stated previously, drum 22 is threadably engaged onto the threaded portion 26 of shaft 27. In addition, crank 30 is received in hole 32 and urges drum 22 to retract cable 16 because of the action of rewind spring mechanism 28. In addition to threaded portion 26, shaft 27 further includes a flange 60, a smooth shoulder portion 62, and a second threaded portion 64. A nut 66 and washer 68 engage threaded portion 64 to secure shaft 26 to housing 14. Shoulder 62 spaces flange 60 from housing 14 and shoulder 62 and flange 60 provide bearing surfaces for rewind spring mechanism 28.

Referring now more particularly to FIGS. 4a and 4b, rewind spring mechanism 28 includes a smooth-bored hub 69 and flange 70 onto which is rigidly secured eccentric crank 30 and starwheel 42. A slot 76 is provided in hub 69 to receive one end 78 of spring 72. The other end 80 of spring 72 is received on pin 82 of spring retainer plate 74. Plate 74 has an aperture 84 of sufficient diameter to permit passage of starwheel 42 therethrough. Plate 74 also has preferably four folded tabs 86 to restrain the maximum expansion of spring 72. The notches 88 formed as a result of folding tabs 86 preferably secure plate 74 to ribs 90 in housing 14 and hence allow spring assembly 28 to react against housing 14.

Referring to both FIGS. 1 and 4a, the transducer 10 is assembled with a pretension in spring 72 and with clearance between drum 22 and flange 60 to permit relative motion between drum 22 and shaft 26 of both an angular and translational nature. As cable 16 is taken up by transducer 10, at most a single layer of cable is allowed on the smooth surface 44 of drum 22. Any motion of cable 16 external to aperture 18, whether longitudinal or transverse, will result only in a longitudinal motion of cable 16 interior of housing 14 because aperture 18 is fixed in housing 14 and is of relatively small clearance for cable 16. Aperture 18 preferably maintains cable 16 in tangential alignment with drum 22. The spacing of helical wraps of cable 16 on drum 22 is determined by the helical pitch (or axial distance moved for each revolution) of engaging threads in bore 50 and on threaded shaft portion 26. In the preferred embodiment of this invention, the helical pitch of these threads is selected to be somewhat larger than the diameter of cable 16 in order to prevent interference between successive wraps of cable 16 on drum 22.

The invention is not to be taken as limited to all of the details thereof as modifications and variations thereof may be made without departing from the spirit or scope of the invention.

What is claimed is:

1. In a continuous source to image distance monitor for use in self-adjusting X-ray equipment utilizing a housing having an aperture fixed therein for receiving a distance measuring wire maintained in tension by a takeup spring, the improvement in combination therewith comprising:

a self traversing, smooth-surfaced constant-diameter takeup cylinder receiving a tension-maintaining torque through an eccentric link means connected to said takeup spring and constrained to move in a helical motion past said housing aperture as said wire moves through said aperture so that said wire is wound in a single layer on said cylinder.

2. The improved combination of claim 1 wherein said wire is wound in a substantially constant helical pattern on said cylinder.

3. The improved combination of claim 2 wherein the single layer of wire on said cylinder has a helical pitch equal to or greater than the diameter of said wire.

4. The improved combination of claim 1 wherein said eccentric link means further comprises means to rotate the moveable element of an electrical potentiometer in direct proportion to longitudinal motion of said cable.

5. In a continuous source to image distance transducer for use in automatic adjusting X-ray radiography equipment having a cable attached at one end within the transducer and at the other end to a relatively moveable portion of the X-ray equipment and a rewind spring to maintain cable tension, the improvement in combination therewith comprising:

A. a housing defining an aperture which is stationary with respect to said housing and adapted to:
  i. permit longitudinal motion of said cable in response to relative displacement between said housing and said relatively moveable portion, and
  ii. prevent transverse displacement of said cable within said housing in response to transverse displacement of said cable exterior to said housing; and
B. a smooth-surfaced drum means for level-winding said cable thereon by combined rotation and translation of said drum means with respect to said aperture; and
C. an eccentric crank means driven by said rewind spring and rotationally urging said drum means in a direction to maintain tension in said cable.

6. The improved combination of claim 5 wherein said drum means rotation and translation is a uniform helical motion.

7. The improved combination of claim 6 wherein said uniform helical motion is proportioned to translate said drum means a distance at least equal to the diameter of said cable for one revolution of said drum means.

8. The improved combination of claim 5 wherein said drum means further comprises an internally threaded axial bore received in mating engagement with an externally threaded shaft secured concentrically within said housing so that said drum means is constrained to rotate and translate by relative motion of the mating threads.

9. The improved combination of claim 5 wherein said crank means further comprises means to rotate the moveable element of an electrical potentiometer in direct proportion to longitudinal motion of said cable.

* * * * *